United States Patent [19]

Yabe

[11] Patent Number: 4,779,130
[45] Date of Patent: Oct. 18, 1988

[54] ENDOSCOPE HAVING A SOLID-STATE IMAGE SENSOR AND SHIELD THEREFOR

[75] Inventor: Hisao Yabe, Tokyo, Japan

[73] Assignee: Olympus Optical Co., Ltd., Japan

[21] Appl. No.: 108,282

[22] Filed: Oct. 14, 1987

Related U.S. Application Data

[62] Division of Ser. No. 813,146, Dec. 24, 1985.

[30] Foreign Application Priority Data

Jan. 14, 1985 [JP] Japan .................................. 60-4392

[51] Int. Cl.[4] .......................... A61B 1/04; A61B 1/06; H04N 7/18
[52] U.S. Cl. ......................................... 358/98; 128/4; 128/6; 358/213.11
[58] Field of Search ................ 358/98, 213.11, 213.13; 128/4, 6

[56] References Cited

U.S. PATENT DOCUMENTS

| 4,491,865 | 1/1985 | Danna ................................... 358/98 |
| 4,573,450 | 3/1986 | Arakawa ............................... 358/98 |
| 4,575,805 | 3/1986 | Moermann ........................... 128/776 |
| 4,639,772 | 1/1987 | Sluyter ................................... 358/98 |
| 4,646,721 | 3/1987 | Arakawa ............................... 128/6 |
| 4,677,471 | 6/1987 | Takamura ............................. 358/98 |

Primary Examiner—Howard W. Britton

[57] ABSTRACT

An endoscope includes an insertion section inserted into the patient's body. A distal end member is provided at the distal end of the insertion section. An illuminating system for illuminating a desired portion is attached to the end member. An observation unit is detachably attached to the distal end member. This unit includes a cylindrical support ditachably fitted to the end member. In the support are disposed an objective lens system for imaging an optical image of the portion illuminated by the illuminating system, a solid-state image sensor for converting the image to an electric signal, and electronic components connected to the sensor.

9 Claims, 3 Drawing Sheets

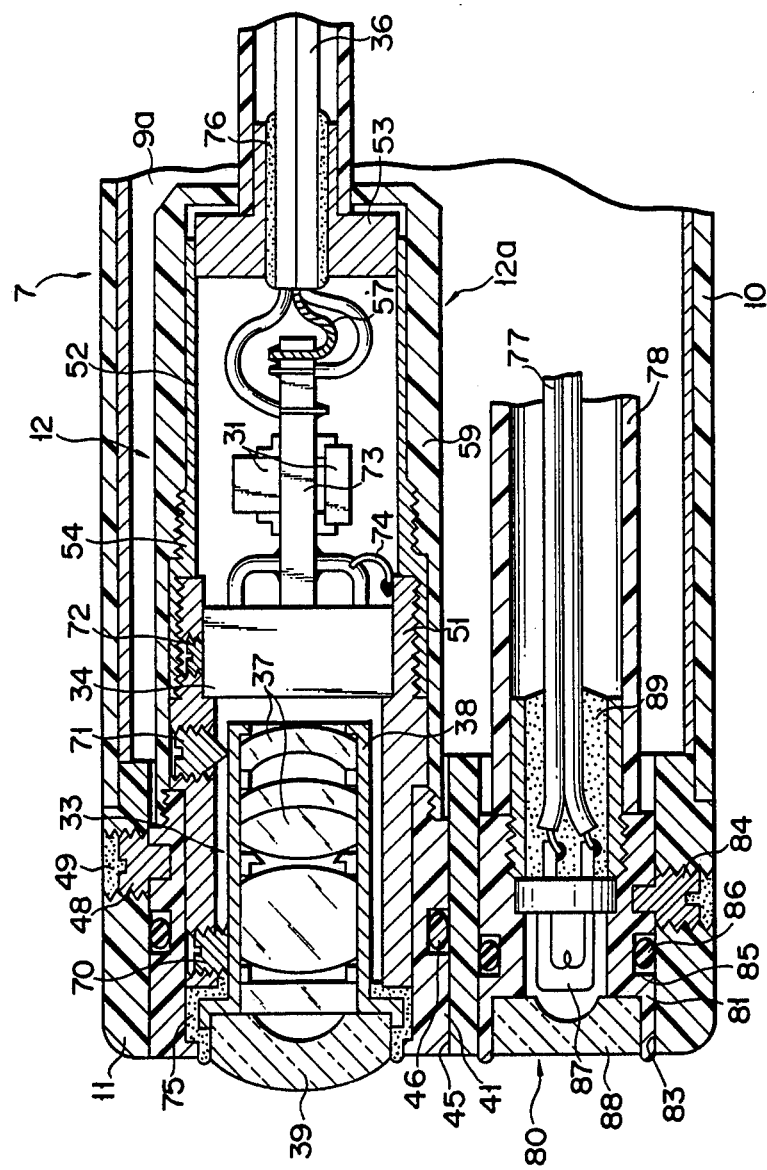

ENDOSCOPE HAVING A SOLID-STATE IMAGE SENSOR AND SHIELD THEREFOR

This is a division of application Ser. No. 813,146, filed Dec. 24, 1985.

BACKGROUND OF THE INVENTION

The invention relates to an endoscope and, more particularly, to an endoscope provided with an electronic components such as a solid-state image sensor at a distal end of the insertion section.

Recently, developments of multi-functional, electronic endoscopes are in progress. For instance, an endoscope with a solid-state image sensor as observing means has been provided. The endoscope with a solid-state image sensor or like electronic component should be assembled carefully. In a prior art method of assembly, a channel tube, liquid and gas supply tubes, etc. are assembled at the distal end of the insertion section of the endoscope, and then an objective lens and the solid-state image sensor are assembled at the distal end. A lightguide or the like is also mounted in the distal end portion before or after the mounting of the solid-state image sensor. This assembly requires an extremely clean environment to avoid attachment of dust to the image sensing surface of the image sensor and also a charging countermeasure to avoid rupture of the image sensor due to static electricity. However, it is infeasible from the standpoint of equipment cost to provide the environment and countermeasure noted above for the entire process of assembly of the endoscope.

Since solid-state lubricant is greatly used in the process of assembling the endoscope, it is necessary to vary the operating environment for each assembling step. Further, the disassembly and repair of the endoscope require operating environments with dust and static electricity countermeasures. It is impossible from the cost stand point to install repair factories with such equipment throughout Japan or all over the world, that is, the number of such repair factories is limited. Therefore, once there occurs a trouble in the endoscope, it takes considerable time to transport the endoscope to the repair factory and make repair.

Further, the solid-state image sensor is mounted in the distal end portion after the channel tube, liquid and gas supply tubes, etc. are assembled. Therefore, it is difficult to make accurate focus adjustment of the image sensor. Further, it is difficult to shield and insulate the image sensor or make shield and insulation tests. Naturally, the reliability of such shield and insulation is inferior.

SUMMARY OF THE INVENTION

The present invention is contrived in consideration of the above circumstances, and intended to provide an endoscope, which permits simplification of the control of production process and the repair, simplification of the production equipment and improvement of quality.

To attain the above object, with the endoscope according to the invention an optical lens system for imaging an optical image and a solid-state image sensor for converting the optical image into an electric signal are combined into an observation unit, which is detachably attached to a distal end portion of the insertion section of an endoscope.

BRIEF DESCRIPTION OF THE DRAWINGS

FIGS. 1 and 2 illustrate an endoscope according to a first embodiment of the invention, in which:
FIG. 1 is a schematic sectional view showing the entire endoscope; and
FIG. 2 is an enlarged sectional view showing a distal end portion of the insertion section of the endoscope; and
FIG. 3 is a sectional view showing a distal end portion of the insertion section of an endoscope according to a second embodiment of the invention.

DETAILED DESCRIPTION OF THE PREFERRED EMBODIMENTS

Preferred embodiments of the invention will now be described.

Figure 1:
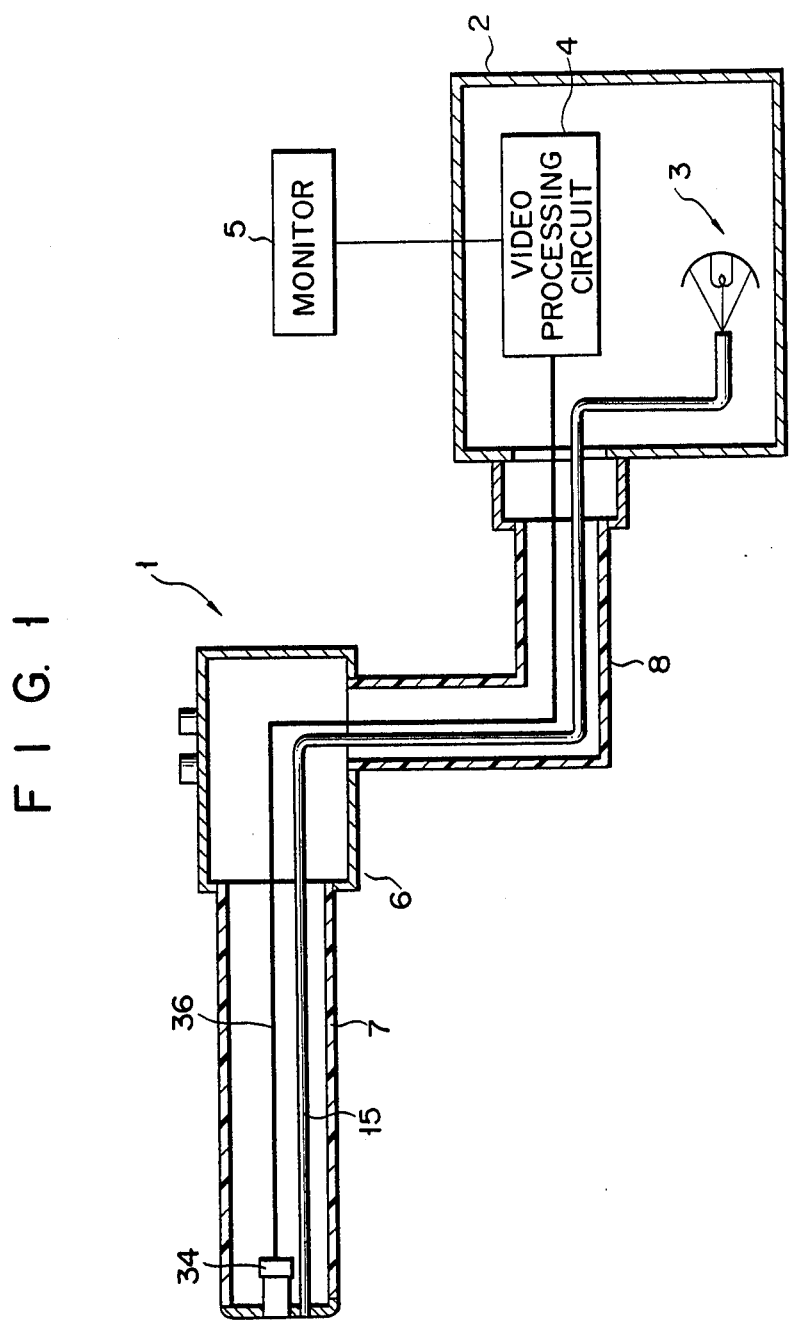

FIG. 1 shows an endoscope embodying the invention. The endoscope comprises an endoscope body 1 and controller 2 connected thereto. Controller 2 includes light source 3 and video processing circuit 4. Video processing circuit 4 is connected to monitor 5 provided outside the controller. Endoscope body 1 has operating section 6, end insertion section 7 extending from operating section 7 and universal code 8 extending from operating section 6 and connected to controller 2.

Figure 2:
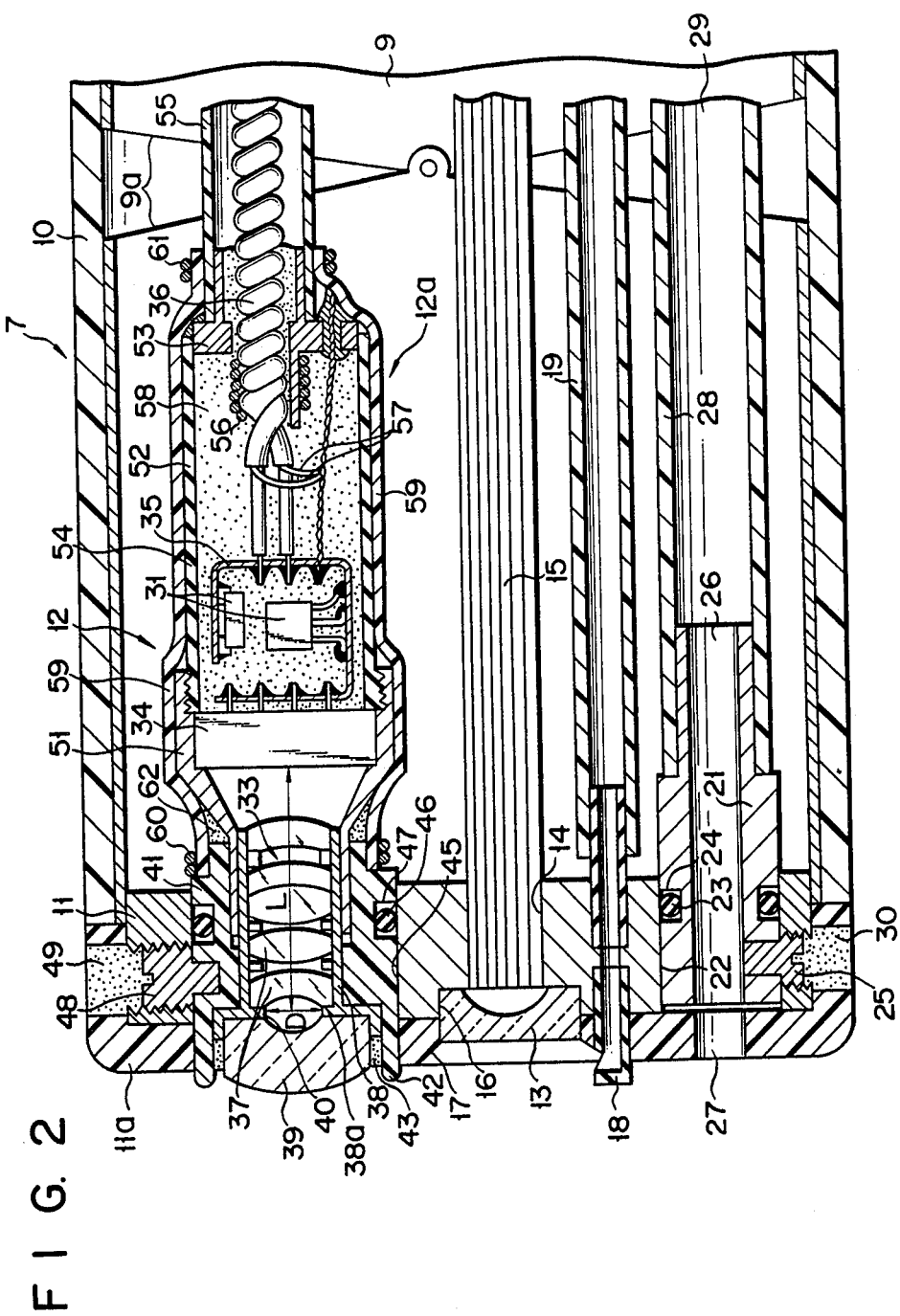

FIG. 2 shows a distal end portion of insertion section 7. Insertion section 7 includes core tube 9 consisting of a plurality of tubular cores 9a rotatably coupled end-to-end to one another and a sheathe 10 made of an electrically insulating synthetic resin and covering the outer periphery of core tube 9. Distal end member 11 is secured to the distal end of insertion section 7 to close the end opening thereof. Distal end member 11 may be made of a metal, a synthetic resin or a ceramic material.

End cover 11a made of an electrically insulating material covers the outer surface of member 11. Observation unit 12 to be described later in detail is detachably mounted in distal end member 11. Illumination lens 13 is airtightly secured to member 11 in a side-by-side relation to observation unit 12. Illumination lens 13 is fitted in recess 16 formed in distal end member 11 and bonded to the same. Distal end member 11 has through hole 14 communicating with recess 16. An end portion of lightguide 15 consisting of an optical fiber bundle is airtightly fitted in through hole 14 and optically coupled to illumination lens 13. Lightguide 15 extends through endoscope body 1 up to light source 3 in controller 2. Cover 11a has hole 17 communicating with recess 16. Hole 17 has a tapered inner periphery. Outer end surface of illumination lens 13 is found deeply inwardly of the outer surface of end cover 11a. Illuminating light supplied from light source 3 and emitted through lightguide 15 and illumination lens 13 thus is prevented by the inner peripheral surface of hole 17 from being directly incident on observation unit 12. It is thus possible to prevent flare. Liquid/gas supply nozzle 18 extends outward through distal end member 11 and end cover 11a. Nozzle 18 is made of an electrically insulating material. Liquid/gas supply tube 19 is connected to the inner end of nozzle 18.

Distal end member 11 has through hole 22 in which cylindrical channel member 21 is fitted. The outer periphery of channel member 21 is formed with annular groove 24 in which O-ring 23 is fitted. Channel member 21 is thus hermetically fitted in through hole 22 with O-ring 23. Channel member 21 is secured to distal end member 11 by set screw 25 screwed sidewise into member 11. End cover 11a has a through hole, through which screw 25 is inserted and which is sealed by electrically insulating bonding agent 30. End cover 11a has through hole 27 communicating with passage 26 defined in channel member 21. Channel tube 28 extending through insertion 7 is connected to channel member 21. Through hole 27, passage 26 and channel tube 28 constitute insertion channel 29. Various tools may be inserted through channel 29.

Observation unit 12 includes substantially cylindrical support 12a detachably fitted to distal end member 11. Assembled in support 12a are objective lens system 33, solid-state image sensor 34, flexible circuit board 35 connected thereto and electric code 36 connected to board 35. Electronic components 31 such as transistor, capacitor, resistor, etc. are mounted on flexible board 35.

Objective lens system 33 includes cylindrical lens frame 38 made of a metal and a plurality of lenses 37 coaxially and hermetically secured to lens frame 38. Observation cover lens 37 is secured to the end of lens frame 38. Lens frame 38 has partition wall 38a which is found between cover lens 39 and lenses 37 and has stop hole 40. Substantially cylindrical cover 41 made of an electrically insulating material is hermetically fitted on the outer periphery of lens frame 38. Cover 41 is detachably and airtightly fitted in through hole 45 formed in distal end member 11 and end cover 11a. The outer periphery of cover 41 is formed with annular groove 47. O-ring 46 is fitted in groove 47 and is in hermetical contact with the inner surface of through hole 45. Cover 41 is secured in a predetermined position by set screw 48 screwed sidewise into distal end member 11. End cover 11a has a hole, through which screw 48 is inserted and which is sealed by electrically insulating bonding material 49.

With cover 41 secured to distal end member 11, cover lens 39 pro3ects outwardly from end cover 11a. Cover 41 has end portion 42 extending outwardly beyond cover lens 39. This end portion 42 serves to prevent illuminating light emitted from illumination lens 13 from being incident on objective lens system 33 through cover lens 39, thus preventing flare. Bonding material 43 fills the gap defined between the outer periphery of cover lens 39 and inner periphery of end portion 42 of cover 41. Thus, lens frame 38 is not exposed to the outside.

Solid-state image sensor 34 is secured to the inner surface of element frame 51. Element frame 51 is a stepped cylinder. Image sensor 34 is arranged in the large diameter portion of element frame 51. The outer diameter of the large diameter portion is greater than the outer diameter of lens frame 38. The small diameter portion of element frame 51 is coaxially fitted on the outer periphery of a rear portion of lens frame 38 and is bonded by a conductive bonding agent to the lens frame. Cover 41 covers the outer periphery of the small diameter portion of element frame 51 as well.

Shield pipe 52 has one end connected to the large diameter portion of element frame 51 and extends coaxially with element frame 51. Shield pipe 52 is made of a metal and is electrically connected to element frame 51. Flexible board 35 which is connected to solid-state image sensor 34, is disposed in shield pipe 52. Electric code securement member 53 made of a metal is fixed to the rear end of shield pipe 52 and electrically connected thereto. Electric code 36 which is connected to flexible board 35, extends rearwardly through shield pipe 52 and securement member 53. Lens frame 38, element frame 51, shield pipe 52 and securement member 53 are electrically connected together and constitute a substantially cylindrical shield member 54.

Protective tube 55 is connected to securement member 53 and extends through the endoscope up to controller 2. Electric code 36 extends through protective tube 55 and is connected to video processing circuit 4 in controller 2. Code 36 has its end portion on the side of flexible base 36 secured by wire 56 to securement member 53. Code 36 consists of a plurality of shielded wires. Of the shielded wires, wires 57 constituting the shield are electrically connected to board 35 and securement member 53.

Shield pipe 52 and securement member 53 are filled with electrically insulating bonding material 58. That is, flexible board 35, electronic components 31 and connecting portion of electric code 36 are buried in bonding material 58. Insulating tube 59 of electrically insulating material is closely fitted on the outer periphery of element frame 51 and shield pipe 52. The front end of insulating tube 59 is fitted on the outer periphery of the rear end portion of cover 41 and secured by wire 60 thereto. The rear end of insulating tube 59 is fitted on the outer periphery of protective tube 55 and secured by wire 61 thereto. A space defined by cover 41, element frame 51 and insulating tube 59 is filled with bonding material 62. Insulating tube 59, cover 41 and shield member 54 constitute support 12a of observation unit 12. Bonding materials 30, 43, 49, 58 and 62 are epoxy or silicone, electrically insulating bonding agents.

With the endoscope having the above construction, objective lens system 33, solid-state image sensor 34, flexible circuit board 35 and electronic components 31 are integrally disposed in cylindrical support 12a to constitute a unit. Support 12a, i.e., observation unit 12 as a whole, is detachably fitted to distal end member 11 of the endoscope. Thus, when there occurs a trouble in the observation unit, it is only necessary to replace this unit with a new one, so that the endoscope can be repaired in a short period of time. In addition, since solid-state image sensor and electronic components 31 are shielded and insulated by support 12a, no special environment is required for the replacement of the unit. Further, since this repair is a mere replacement of the observation unit, it does not require any particular skill so that it can be readily done even by a person without any skill. Still further, since the observation unit is replaced as a whole, the reliability of the endoscope will never be reduced by the repair. Yet further, various adjusting operations and tests of focus, resolution, shield, insulation, etc. can be done with the observation unit alone, and the production property of the endoscope can be improved. Further, by providing a uniform size of observation unit, it is possible to permit various observation units with solid-state image sensors having various functions, i.e., zooming, short distance focusing, high sensitivity, to be assembled in a single endoscope. It is thus possible to meet a wide variety of doctor's needs. Particularly, it is possible to assemble the same observation unit in various endoscopes, e.g., one having a large channel system or one having a forcept guide mechanism.

Further, solid-state image sensor 34, flexible board 35 and electronic components 31 are enclosed in shield member 54 including lens frame 38, element frame 51 and shield pipe 52, thereby being shielded against high frequency noise. Therefore, even if a tool for generating a high frequency wave, e.g., electrocautery, is inserted in channel 29 of the endoscope, the solid-state image sensor and electronic components will never be adversely affected by such a high frequency wave.

Further, shield member 54 is electrically insulated by cover 41, bonding material 43, insulating tube 59 and protective tube 55. Thus, even when a large current is caused from video processing circuit 4 to flow into observation unit 12 with the insertion section of endoscope inserted in the patient's body, the patient will never be struck by electricity.

Further, solid-state image sensor 34, electronic components 31 and connecting portion of electric code 36 are buried in bonding material 58 and perfectly sealed with respect to the outside. Thus, even when the relative humidity in the insertion section 7 is increased with the endoscope immersed in an antiseptic solution for long time, condensation on the solid-state image sensor, electronic components and connecting portion of electric code is prevented.

Usually, the endoscope is exposed to ethylene oxide gas atmosphere for disinfection. In this situation, deterioration or rupture of electronic components in the endoscope is liable to result. However, with the above embodiment the interior of observation unit 12 is airtightly sealed and filled with bonding material 58, so that there is low possibility for the ethylene oxide gas to reach the electronic components in the observation unit. Even if ethylene oxide gas should penetrate insulating tube 59 made of resin and bonding material 58, the concentration of ethylene oxide gas reaching solid-state image sensor 34 is too low to pose any problem.

Further, in the above embodiment solid-state image sensor 34 and cover lens 39 are spaced apart by adistance equal to length L of lens frame 38, which constitutes part of shield member 54. In addition, diameter D of stop hole 40 for passing light is very small compared to length L of lens frame 38. Thus, noise entering from the side of lens cover 39 can be sufficiently blocked with respect to solid-state image sensor 34. Further, in an industrial endoscope the grounding terminal may be exposed to the outside. Therefore, where lens frame 38 constitute part of shield member 54, observation unit 12 need not be provided with any electric insulation means.

Further, the inner surface of hole 17 surrounding illumination lens 13 and end portion 42 of cover 41 prevent illuminating light emitted from illumination lens 13 from being directly incident on objective lens system 33. It is thus possible to prevent flare. As alternative flare prevention means, a partition wall may be provided between illumination lens 13 and cover lens 39.

FIG. 3 shows a second embodiment of the invention. In FIG. 3, parts like those in the preceding first embodiment are designated by like reference numerals, and only a portion of this embodiment that is different form the first embodiment will be described in detail.

In this embodiment, distal end member 11 is made of an electrically insulating material, and observation unit 12 can be pulled out the end member. More specifically, insulating tube 59 has a smaller outer diameter than the outer diameter of cover 41 fitted in through hole 45 formed in distal end member 11. Lens frame 38 is supported by element frame 51 through three inclination angle ad3usting screws 70 and three centering screws 71. Lens frame 38 and objective lens system 33 disposed therein thus can be adjusted for inclination angle by adjusting screws 70 and centered by centering screws 71 with respect to solid-state image sensor 34. Lens frame 38 and element frame 51 are electrically connected together by adjusting screws 70. Solid-state image sensor 34 is secured by screw 72 to element frame 51. Terminals of image sensor 34 are bent and connected to circuit board 73. A grounding terminal of image sensor 34 is connected to element frame 51 via lead 74. Insulating tube 59 is screwed on both shield pipe 52 and cover 41. Shield memer 54 is sealed at front and rear ends by bonding materials 75 and 76 and has a sealed inner space, which is filled with a gas not containing hydrogen and oxygen, i.e., an inert gas. Dry air may be sealed in lieu of the inert gas. Element frame 21, shield pipe 52 and securement member 53 are bonded together by a conductive bonding agent, and they are electrically connected together.

In the second embodiment, lamp unit 80 as illumination system is detachably attached to distal end member 11. Lamp unit 80 has substantially cylindrical unit body 81 made of electrically insulating material which is detachably fitted in through hole 83 formed in distal end member 11. The outer periphery of body 81 is formed with annular groove 85, in which O-ring 86 is fitted. O-ring 86 is in hermetical contact with the inner surface of through hole 86. Body 81 is secured by set screw 84 to distal end member 11. Lamp 87 is disposed in body 81. The front open end of body 81 is hermetically closed by cover lens 88. Protective tube 78 is connected to body 81, and electric code 77 connected to lamp 87 is led through protective tube 78. A rear end portion of body 81 is filled with electrically insulating bonding material 89. Portion of electric code 77 connected to lamp 87 is buried in bonding material 89.

With the second embodiment of the above construction, the following functions and effects can be obtained in addition to the functions and effects obtainable with the first embodiment.

Observation unit 12 can be pulled out insertion section 7 of the endoscope. Therefore, when a trouble occurs in observation unit 12, this unit can be easily replaced without processing the insertion section of the endoscope. Observation unit 12 is replaced in the following way. First, bonding material 49 is scraped off distal end member 11. Then, set screw 48 is removed. Subsequently, observation unit 12 is withdrawn forwardly out of distal end member 11 using a suction tool. Then, insulating tube 59 is removed rearwardly from shield pipe 52 and element frame 51 by turning it. Then, shield pipe 52 is cut at a position near securement member 53. Electric code 36 is then removed from circuit board 73. Securement member 53 is then removed from shield pipe 52. Thereafter, a new observation unit is connected to electric code 36 and securement member 53.

Lamp unit 80 is detachably fitted to distal end member 11 and can be pulled uut. Therefore, when a disconnection occurs in illumination lamp 87, illumination unit 80 can be readily replaced.

Further, since the position of lens frame 38 is adjustable by inclination angle adjusting screws 70 and centering screws 71, it is possible to provide the performance of objective lens system 33 to the utmost.

It is to be further noted that in observation unit 12 of the subject endoscope, image sensor 34 is located such that is light-receiving surface is substantially perpendicular to the axis of insertion section 7, and circuit board 73, on which electronic components 31 associated with image sensor 34 are mounted, is located substantially parallel to the axis of insertion section 7.

In an endoscope disclosed for example in U.S. Pat. No. 4,491,865 to Danna et al (an example of a conventional endoscope), the image sensor and the circuit board, on which electronic components associated with the image sensor are mounted, are located perpendicular to the axis of the insertion section. No only the electronic components but also the external leads of the image sensor and the signal pickup leads are arranged on the circuit board. Therefore, if the electronic components are large in size or if the external leads and signal pickup cords are large in number, it is necessary to increase the surface area of the circuit board. If the surface area of the circuit board is increased, the diameter of the insertion section will also increase. It should be noted that the used of a large-diameter insertion section may sometimes cause a very serious problem.

In the present invention, the circuit board extends, in the axial direction of the insertion, from the image sensor toward the proximal end of the insertion section. With this construction, if only the circuit board is lengthened in the axial direction of the insertion section, the surface area of the circuit board can be increased without increasing the diameter of the insertion section. In the present invention, furthermore, the circuit board has three regions, namely a first region used for the connection of the external leads of the image sensor, a second region used for the mounting of electronic components, and a third region used for the connection of electric cords. The first to third regions are arranged in order from the image sensor toward proximal end of the insertion section. (The region is closest to the image sensor, the third region is closest to the proximal end of the insertion section, and the second region is located between the first and third regions). With this construction, the externalleads, electronic components, and signal pickup cords can be connected to the circuit board or mounted thereon without being obstructed by one another. As a result, the operations for connecting the signal lines and mounting the electronic components can be performed with ease. Simultaneously, the size of the circuit board can be prevented from increasing in the radial direction of the insertion section.

In the present invention, the circuit board has two surfaces parallel to each other. These two surfaces can be used for the connection of the external leads and signal pickup cords or for the mounting of the electronic components. By properly arranging the external leads (or signal pickup wires, or electronic components) on these two different surfaces, the number of members connected or mounted on one surface can be decreased. In other words, the area of each surface can be reduced. As a result, the size of the circuit board can be decreased in the axial direction of the insertion section. In Danna et al U.S. Pat. No. 4,491,865 in contrast, the image sensor and the cicuit board face each other and are located such that they are perpendicular to the axis of the insertion section. Admittedly, even with the construction of the reference, the electronic components can be arranged on the two surfaces of the circuit board. However, the external leads of the image sensor must be connected only to that surface of the circuit board which faces the image sensor, and the signal pickup cords must be connected only to the opposite surface of the circuit board.

What is claimed is:

1. an endoscope comprising:
   an operation section;
   an insertion section extending from the operation section and having a proximal end, a distal end, and a central axis;
   an observation unit located at the distal end of the insertion section, the observation unit including:
   an objective lens system for focusing an optical image;
   a solid-state image sensor for converting the optical image focused by the objective lens system to an electric signal, the solid-state image sensor having a light-receiving surface located substantially perpendicular to the central axis of the insertion section, for receiving the optical image from the objective lens system;
   a circuit board electrically connected to the image sensor, the circuit board being located between the image sensor and the proximal end of the insertion section and extending substantially parallel to the central axis of the insertion section;
   a plurality of electronic components mounted on the circuit board and electrically connected to the image sensor;
   an electric cord connected to the circuit board to pick up the electric signal and support means covering the objective lens system, solid-state image sensor, and circuit board, and having a shield member for shielding the solid-state image sensor and electronic components against high frequency waves.

2. An endoscope according to claim 1, wherein the light-receiving surface of the image sensor has a center and the circuit board is located in a plane passing through the center of the light-receiving surface.

3. An endoscope according to claim 1, wherein the shield member is closed airtightly.

4. An endoscope according to claim 1, wherein the shield member includes a substantially cylindrical lens frome for covering the objective lens system, a substantially cylindrical element frame coaxially connected to the lens frame and covering the solid-state image sensor, and a substantially cylindrical shield pipe coaxially connected to the element frame and covering the electronic components, the lens frame, element frame and shield pipe being electrically connected together.

5. An endoscope according to claim 1, wherein said electric cord includes a lead wire which has a tip end connected to the circuit board, and an outer sheath which is formed around the lead wire and part of which is secured to the support means.

6. An endoscope according to claim 1, wherein said support means includes an insulating member fitted around the shield member, for providing electric insulation from the outside.

7. An endoscope according to claim 1, wherein said image sensor includes a plurality of external leads, and the circuit board includes first region to which the external leads are coneected, a second region on which the electronic components are mounted, and a third region to which the electric cord is connected, the first to third regions being arranged in order from the image sensor toward the proximal end of the insertion section.

8. An endoscope according to claim 7, wherein the circuit board includes a first surface having the first to third regions and extending substantially parallel to the central axis of the insertion section, and a second surface having at least one of the first to third regions and extending substantially parallel to the central axis of the insertion section.

9. An endoscope according to claim 8, wherein the second surface includes the first to third regions.

* * * * *